United States Patent
Lee et al.

(10) Patent No.: US 7,718,202 B2
(45) Date of Patent: May 18, 2010

(54) METHOD FOR TREATING ERECTILE DYSFUNCTION WITH ACANTOPANAX EXTRACT (OGALPI)

(75) Inventors: Jung Joon Lee, Taejeon-si (KR); Jeong-Hyung Lee, Taejeon-si (KR); Young Soo Hong, Taejeon-si (KR); Young Ho Kim, Taejeon-si (KR); Young Deuk Choi, Seoul (KR)

(73) Assignee: Korea Research Institute of Bioscience and Biotechnology, Taejeon (KR)

(*) Notice: Subject to any disclaimer, the term of this patent is extended or adjusted under 35 U.S.C. 154(b) by 0 days.

(21) Appl. No.: 12/240,503

(22) Filed: Sep. 29, 2008

(65) Prior Publication Data

US 2009/0022822 A1    Jan. 22, 2009

Related U.S. Application Data

(63) Continuation of application No. 10/571,195, filed on Mar. 8, 2006, now abandoned.

(30) Foreign Application Priority Data

| Sep. 15, 2003 | (KR) | ........................ 10-2003-0063728 |
| Sep. 14, 2004 | (WO) | ................ PCT/KR2004/002338 |

(51) Int. Cl.
*A61K 36/254* (2006.01)
*A61K 36/00* (2006.01)

(52) U.S. Cl. ..................... 424/728; 424/773; 424/779; 424/725

(58) Field of Classification Search ........................ None
See application file for complete search history.

(56) References Cited

U.S. PATENT DOCUMENTS 5,378,466 A    1/1995    Endo

FOREIGN PATENT DOCUMENTS

| JP | 2000-319191 | 11/2000 |
| JP | 2000-319191 A | 11/2000 |
| KR | 2000-0074868 | 12/2000 |
| KR | 2000-0074869 | 12/2000 |
| KR | 2001-0009653 | 2/2001 |
| KR | 2001-0019397 | 3/2001 |

OTHER PUBLICATIONS

Oh et al. Two 3,4-Seco-Lupane Triterpenes From Leaves of *Acanthopanax divaricatus* Var. *Albeofructus*; Chem. Pharm. Bull., 2000, 48(6) pp. 879-881.*
Phillipson, J. New Drugs From Nature—It Could Be Yew; Phytotherapy Research 13 (1999) pp. 2-8.*

(Continued)

*Primary Examiner*—Patricia Leith
(74) *Attorney, Agent, or Firm*—Lucas & Mercanti, LLP (57) ABSTRACT

The present invention relates to an alcohol extract of ogalpi, erectile dysfunction improving health food and a treating agent containing the same, more precisely, an alcohol extract of ogalpi having an effect of improving erectile dysfunction, erectile dysfunction improving health food and an erectile dysfunction treating agent containing the same. The alcohol extract of ogalpi of the present invention has a promoting effect of penile erectility, so that it can be effectively used for the improvement of erectile dysfunction.

12 Claims, 4 Drawing Sheets

OTHER PUBLICATIONS

Revilla et al. Comparison of Several Procedures Used for the Extraction of Anthocynains From Red Grapes; J. Agric. Food Chem. 1998, 46, pp. 4592-4597.*

Lin, CC et al., Antioxidant and Hepatoprotective Effects . . . , Phytotherapy Resarch, Phytother. Res., 2000, 14:489-494.

Heaton, JPW et al., Sequential Administration . . . , Rapid Communication International, Journal of Impotence Research, 2002, 14:61-64.

Huang, KC, The Pharmacology of Chinese Herbs, CRC Press, 1992, pp. 46-48.

Tang, W et al., Chinese Drugs of Plant Origin: Chemistry, Pharmacology, and Use in Traditional and Modern Medicine, Springer, 1992, pp. 1-12.

Burnett AL, Nitric Oxide in the Penis: Physiology and Pathology, Journal of Urology, 1997, 157:320-324.

Burnett AL et al., Nitric Oxide: A Physiologic Mediator of Penile Erection, Science, 1992, 257:401-403.

Gonzalez-Cadavid NF et al., Nitric Oxide and the Cyclic GMP System in the Penis, Mol. Urol., 1999, 3:51-59.

Christ GJ et al., Pharmacological Studies of Human Erectile Tissue: Characteristics of Spontaneous . . . , Br. J. Pharmacol., 1990, 101:375-81.

Fovaeus M et al., Effects of Some Calcium Channel Blockers on . . . , Journal of Urology, 1987, 138:1267-1272.

Karaki H et al., Calcium Movements, Distribution, and Functions in Smooth Muscle, Pharmacological Review, 1997, 49:157-230.

Kim N. et al., A Nitric Oxide-like Factor Mediates Nonadrenergic-Noncholinergic . . . , J. Clin. Invest, 1991, 88:112-118.

Nishiyama N et al., Effect of Eleutherococcus Senticosus and Its Components on Sex-and Learning-Behaviors and . . . , Shoyakugaku Zasshi, 1985, 39:238-242.

Oh, O-J et al., Two 3,4-seco-Lupane Triterpenes from Leaves of Acanthopanax . . . , Chem. Pharm. Bull., 2000, 48 (6):879-881.

Kang, J et al., Quantitative Determination Eleutheroside B and E from Acanthopanax . . . , Arch. Pharm. Res., 2001, 24 (5): 407-411.

The International Search Report (ISR) dated Dec. 27, 2004 and International Preliminary Examination Report (IPER) dated Jan. 3, 2006 corresponding PCT/KR2004/002338.

Jung, et al., Dohae Hyangyak Desajeoun—Selected 100 Species of Plants Classification into Plants-, pp. 432-435, 1990.

* cited by examiner

METHOD FOR TREATING ERECTILE DYSFUNCTION WITH ACANTOPANAX EXTRACT (OGALPI)

CROSS-REFERENCE TO RELATED APPLICATION

This application is a continuation application of U.S. patent application Ser. No. 10/571,195 filed Mar. 8, 2006, which is a 371 of PCT Application Serial No. PCT/KR2004/002338 filed Sep. 14, 2004 which claims benefit of foreign priority to Korean Patent Application No. 10-2003-0063728 filed Sep. 15, 2003, the contents of each of which are incorporated herein by reference in its entirety.

TECHNICAL FIELD

The present invention relates to an extract of ogalpi, more precisely, an alcohol extract of ogalpi having an effect of improving erectile dysfunction and erectile dysfunction improving health food and an erectile dysfunction treating agent containing the same.

BACKGROUND ART

The penile erection, coming through a complicated physiological pathway involved in not only blood vessel system but also endocrine and nervous system, is induced by a chain of phases such as relaxation of corpus cavernous smooth muscle by a variety of stimuli, increase of blood flow by the inflation of a small hole and the expansion of an arteriole, increase of the inside pressure of the penis, decrease of the venous outflow by compressing of the subtunical venular plexuses between the tunica albuginea and the peripheral sinusoids, and then increase of the inner pressure of the penis more (Lue T F, Tanagho E A., *J Urol,* 1987, 137, 829-36). With the physiological explanation of the penile erection and the studies on the medicinal effects and mechanism of many agents applying to corpus cavernous smooth muscle, an attempt has been made to apply those medicines having an activity of relaxing corpus cavernous smooth muscle to the treatment of erectile dysfunction. As of today, known agents being able to relax corpus cavernous smooth muscle are adrenergic α-receptor blockades, cholines, NO (Nitric Oxide), peptides, prostaglandin, histamines, calcium channel inhibitors, calcium channel openers, nonspecific vasodilators, etc. (Linet O I, Ogrinc F G., *N Eng J Med,* 1996, 334, 873-7; Tong Y C et al., *Pharmacology,* 1992, 45, 241-9; Miller M A et al. *Int J Impot Res,* 1995, 7, 91-100; Andersson K-E, Wagner G., *Physiol Rev,* 1995, 75, 191-236; Andersson K-E, Stief C G., *World J Uro,* 1997, 115, 14-20; Andersson K E., *Pharmacol Rev,* 2001, 53, 417-50).

There has been no report on the frequency of erectile dysfunction. However, the number of patients suffering from erectile dysfunction is definitely being increased by the reasons of the expanded life span, the increase of adult diseases, change of diet, the increase of industrial and traffic accidents, the increase of mental stress and physical fatigue resulted from complicated modern life, etc. The methods for the treatment of erectile dysfunction are internal treatment including taking medicines and male hormones, surgical treatment including vascular surgery, surgical implantation of penile prosthesis, etc, and injection of vasodilators in corpus cavernous smooth muscle. Medicines for the internal treatment, which is, though, not suitable for the treatment of severe stromal erectile dysfunction, are exemplified by male hormones, yohimbin, apomorphine and traszodone. However, such medicines have side effects and even their treating effects are in doubt. A medicine acknowledged to have a reliable reproducibility has not been reported yet (Andersson K E, *Pharmacol Rev,* 2001, 53, 417-50; Montorsi F et al., *BJU International,* 2003, 91, 446-54; Vitezic D, Pelcic J M, *Int J Clin Pharmacol Ther,* 2002, 40(9), 393-403), and just sildenafil has been used for the primary treatment of erectile dysfunction (Heaton J P, Dean J, Sleep D J, *Int J Impot Res,* 2002, 14, 61-4).

Ogalpi has been well known as a traditional medicine in Korea. It has a hot and bitter taste and has a property of warming things up. Ogalpi is known to eliminate gout in liver and nervous system, invigorate and bring the essence in a body. It has been prescribed for such diseases as Oro (fatigue caused by the weakness of five internal organs), Chilsang (seven representative symptoms shown in men caused by the weakness of a body) and difficulty in moving legs. Long-term administration of ogalpi increases energy, protects the stomach, invigorates, clears mind, increases will power, prevents aging, helps having a light heart and clears bad blood in a body. So, ogalpi has been used for the treatment of such symptoms as pain in backbone, male impotence, scrotal eczema, female amenorrhea, etc. In Korea, ogalpi has long been used as a natural tonic medicine, and is still added to health food. It was once reported that an extract of *Acanthopanax senticosus* had liver protective activity (Chun-Ching Lin and Pei-Chen Huang, *Phytotherapy Research,* 2000, 14, 489-494). However, there is no report on the effect of ogalpi on sexual function.

Thus, the present inventors found that extracts of each roots and stems of *Acanthopanax divaricatus* var. *albeofructus, Acanthopanax senticosus, Acanthopanax senticosus* var. *subinermis* and *Acanthopanax koreanum*, extracted by using 70% ethanol or distilled water, induce the penile erection and have completed this invention by confirming that those extracts can be effectively used for the production of health food and a treatment agent for erectile dysfunction.

DISCLOSURE

Technical Problem

It is an object of the present invention to provide an alcohol extract of ogalpi having an effect of improving erectile dysfunction.

It is another object of the present invention to provide health food for the improvement of erectile dysfunction containing an extract of ogalpi as an effective ingredient.

It is a further object of the present invention to provide a treating agent for erectile dysfunction containing an alcohol extract of ogalpi as an effective ingredient.

Technical Solution

In order to achieve the above object, the present invention provides an alcohol extract of ogalpi having an effect of improving erectile dysfunction.

The present invention also provides health food for the improvement of erectile dysfunction containing an extract of ogalpi as an effective ingredient.

The present invention further provides a treating agent for erectile dysfunction containing an alcohol extract of ogalpi as an effective ingredient.

Hereinafter, the present invention is described in detail.

The present invention provides an alcohol extract of ogalpi having an effect of improving erectile dysfunction.

In this invention, ogalpi is preferably selected from a group consisting of *Acanthopanax divaricatus* var. *albeofructus*, *Acanthopanax senticosus*, *Acanthopanax senticosus* var. *subinermis*, and *Acanthopanax koreanum*, and is more preferred to be *Acanthopanax divaricatus* var. *albeofructus*. An extract of ogalpi of the present invention preferably extracted from roots or stems, and more preferably extracted from the stems of ogalpi. Herein, the stem means all the aerial parts except roots.

Alcohol is preferably selected from a group consisting of methanol, ethanol, propanol and butanol, and among them, ethanol is more preferred. The concentration of alcohol is preferably 0~100%, and more preferably 70%.

When an extract extracted from roots or stems of any of *Acanthopanax divaricatus* var. *albeofructus*, *Acanthopanax senticosus*, *Acanthopanax senticosus* var. *subinermis* or *Acanthopanax koreanum* was treated to corpus cavernous smooth muscle of a rabbit, the relaxation of the smooth muscle thereof increased dose-dependently. The relaxation of the corpus cavernous smooth muscle was greater when an extract of *Acanthopanax divaricatus* var. *albeofructus* was treated, and a stem extract had better relaxing effect than a root extract (see FIG. 1a). And in the case of an extract extracted from the stems of ogalpi, 70% ethanol extract had better relaxing effect on corpus cavernous smooth muscle of a rabbit than distilled water extract (see FIG. 1b). When 70% alcohol extract prepared from the stems of *Acanthopanax divaricatus* var. *albeofructus* was orally administered to a white rat, erectibility of the penis of the white rat was increased dose and administration period-dependently (see FIG. 3). Therefore, an extract of ogalpi was proved to increase the penile erection by helping relaxation of corpus cavernous smooth muscle, and among extracts, 70% ethanol extract of the stems of *Acanthopanax divaricatus* var. *albeofructus* was confirmed to have the best relaxing effect.

It is believed that NO (nitric oxide) is involved in the relaxation of corpus cavernous smooth muscle (Burnett A L, *J Urol*, 1997, 157, 320-4; Burnett A L et al., *Science*, 1992, 257, 401-3). NO producer binds to a receptor on the cell membrane of endothelial cells, resulting in the increase of free calcium concentration. The increased number of calcium stimulates the synthesis and the isolation of NO. The isolated NO enters into smooth muscle cells to activate guanylate cyclase of the smooth muscle, resulting in the increase of the production of cGMP. The increase of cGMP induces the relaxation of the smooth muscle (Gonzalez-Cadavid N F, Ignarro L J, Rajfer J, *Mol Urol*, 1999, 3, 51-9). The cooperation of NO and ogalpi in corpus cavernous smooth muscle has not been discovered yet. In the preferred embodiment of the present invention was confirmed that the smooth muscle relaxing effect of HS, a 70% ethanol extract of the stems of *Acanthopanax divaricatus* var. *albeofructus* which has the best relaxing activity, varied with the removal of endothelial cells or administrations of atropine and ODQ inhibiting acetylcholine; methylene blue, a guanylate cyclase inhibitor; pyrogallol, a NO inactivator; and L-NNA, a NO generation inhibitor (see FIG. 1c). Thus, the relaxation of corpus cavernous smooth muscle induced by HS is believed to be involved in endothelial cells and NO as well. When relaxation of corpus cavernous smooth muscle was beginning by HS, cGMP inside of the smooth muscle was increased HS dose-dependently, indicating that HS induced NO involved corpus cavernous smooth muscle relaxation (see FIG. 2).

When corpus cavernous smooth muscle was in a stable condition, HS did not cause relaxation or constriction therein, but just inhibited voluntary activity. The voluntary activity of a smooth muscle cannot be inhibited by a neural medicine in most cases, but is controlled by calcium or potassium contained medicines or a prostaglandin generation inhibitor (Christ G J et al., *Br J Pharmacol*, 1990, 101, 375-81). And HS inhibits voluntary activity, so a 70% ethanol extract of *Acanthopanax divaricatus* var. *albeofructus* stem must affect corpus cavernous smooth muscle directly.

When a slice of a smooth muscle was exposed on potassium-rich nutrients not having calcium, ground tension of the smooth muscle disappeared. But, ground tension was recovered by the addition of calcium, leading to constriction. Such mechanism might be progressed through membrane potential dependent calcium channel that is activated very slowly (Fovaeus M et al., *J Urol*, 1987, 138, 1267-72; Karaki H et al., *Pharmacol Rev*, 1997, 49, 157-230). In the preferred embodiment of the present invention, the lowered ground tension of a smooth muscle stabilized in potassium-rich nutrients not including calcium dropped lower and lower by ES (see Example 2-2). This was resulted from the intracellular movement of calcium, more precisely, the increase of the outflow of intracellular calcium or the increase of the inflow of the calcium into myocytes, meaning the decrease of isolated calcium in cytoplasm, dropped ground tension of a smooth muscle. Constriction to $Cacl_2$ of a smooth muscle stabilized in potassium-rich nutrients without calcium was also decreased by HS dose-dependently. This result indicates that HS inhibits the intracellular calcium movement through membrane potential dependent calcium channel, which is slowly activated, leading to the relaxation of the muscle with the decrease of intracellular calcium content.

Figure 2:
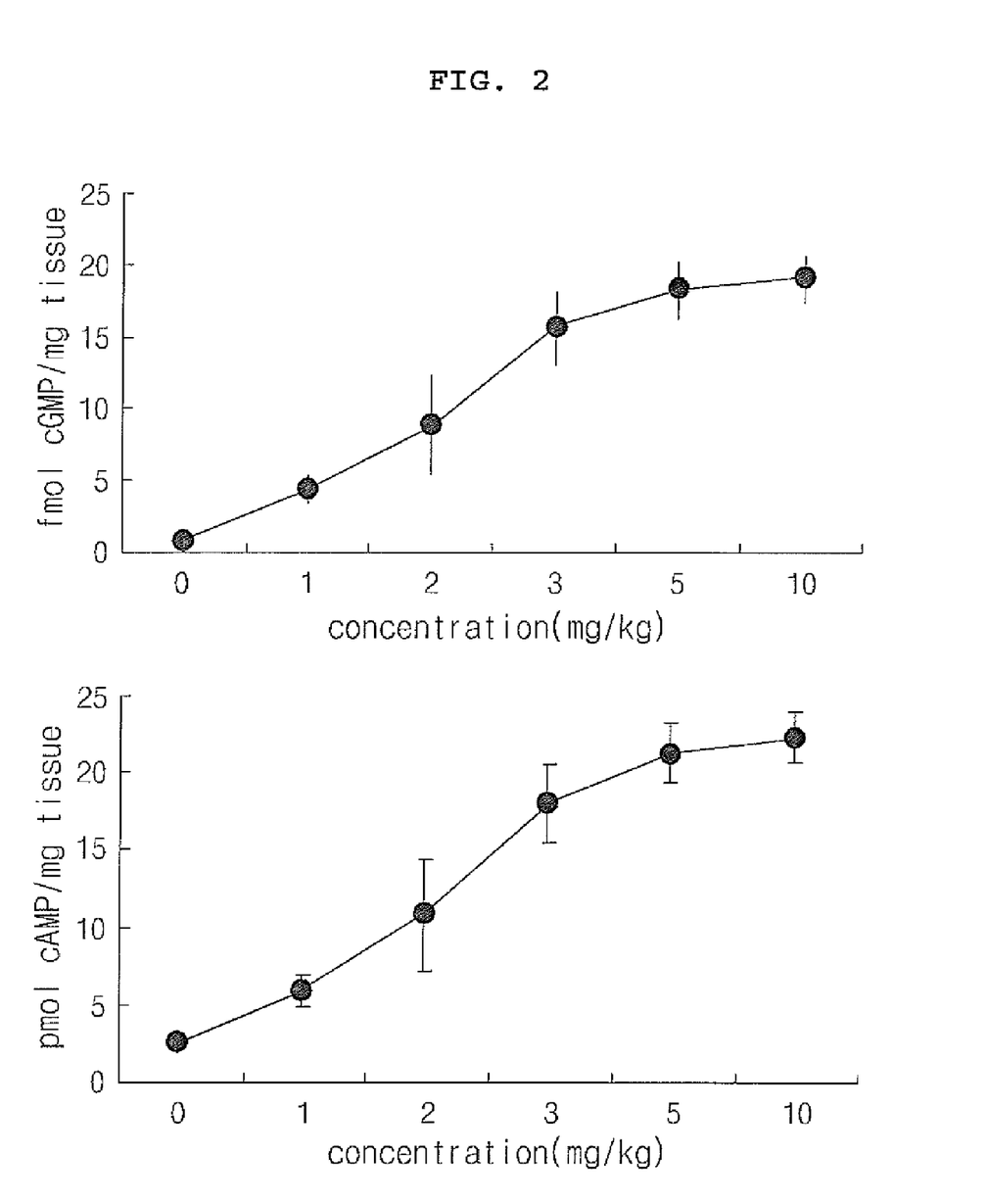
FIG. 2 is a set of graphs showing the changes of cGMP and cAMP concentrations in corpus cavernous smooth muscle of a rabbit after an extract extracted from the stems of ogalpi using 70% ethanol (HS) was treated to the animal at different concentrations.
Figure 4:
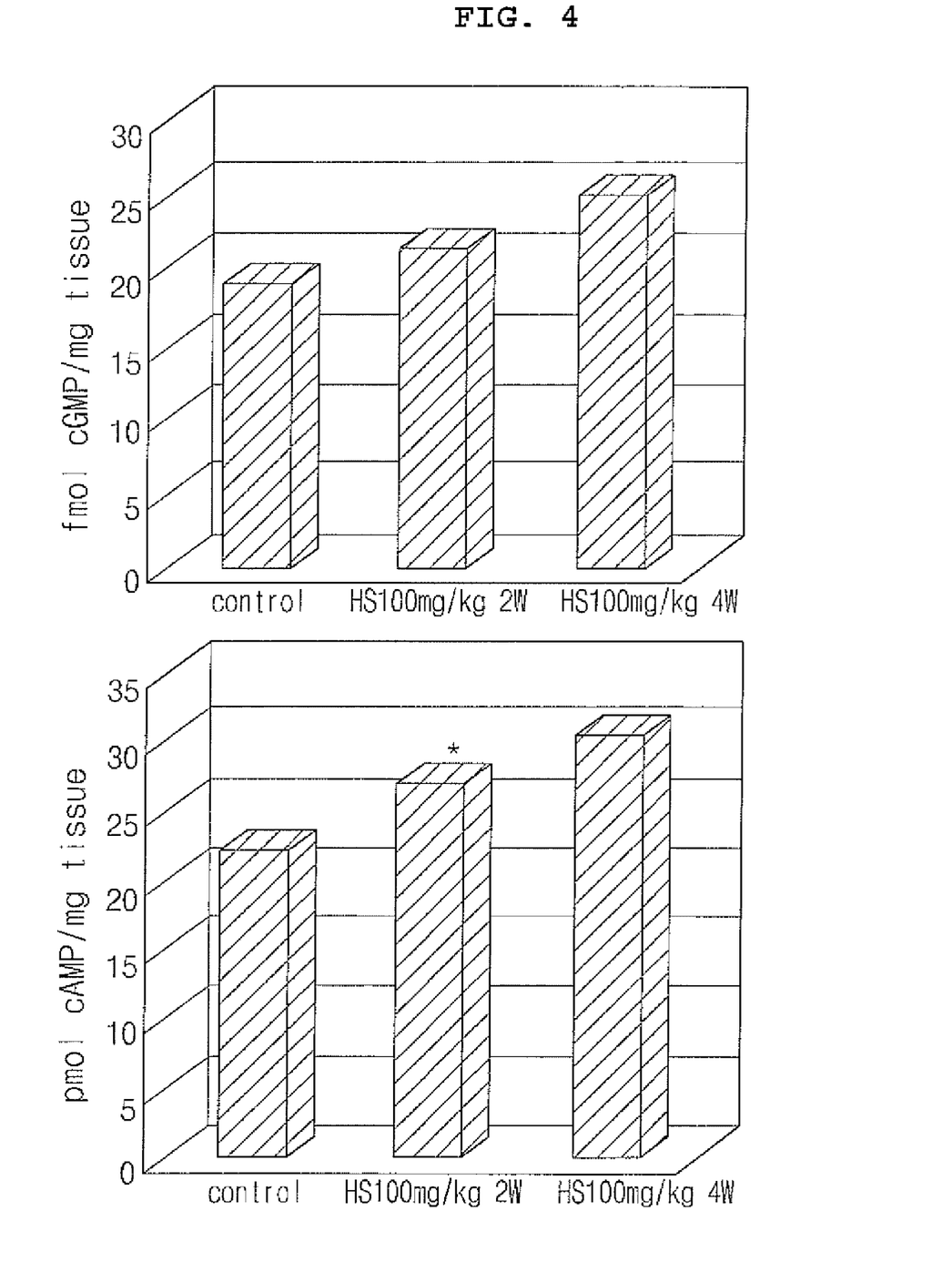
FIG. 4 is a set of graphs showing the changes of cGMP and cAMP concentrations in corpus cavernous smooth muscle of white rats according to the administration times. Precisely, 70% ethanol extract prepared from the stems of *Acanthopanax divaricatus* var. *albeofructus* was orally administered by the dosage of 100 mg/kg for 2 weeks to group 1 and for 4 weeks to group 2, followed by the comparison between the two cases.

In regard to the relaxation of corpus cavernous smooth muscle, HS increased the contents of cGMP and cAMP in corpus cavernosa dose-dependently (see FIG. 2 and FIG. 4). This result indicates that the penile erection induced by HS is involved in not only cGMP related relaxation but also cAMP related relaxation.

The present invention also provides health food for the improvement of erectile dysfunction containing an alcohol extract of ogalpi as an effective ingredient.

An extract of the present invention strongly induced the relaxation of corpus cavernous smooth muscle of a rabbit. When the extract was orally administered to a white rat, the erectility increased dose- and administration time-dependently. Therefore, a composition of the present invention containing an extract of ogalpi as an effective ingredient can be effectively used for the improvement of erectile dysfunction.

An extract of ogalpi of the present invention can be added to food as it is or together with other food or food ingredients, and be formulated by conventional methods. At this time, mixing rate for the effective ingredients is determined by the purpose of use (prevention, improvement or treatment). In general, an extract of ogalpi of the present invention is preferably added to food or beverages by 0.2~20 weight % to that of raw material, more preferably by 0.24~10 weight %. The dose might be less than the above when the extract is administered for long-term to control health condition or simply for health or hygiene. However, the dose can be more than the above even in the case of long-term administration because of the safety of the effective ingredient.

There is no limitation in food applicable to the extract of the present invention. Thus, the extract can be added to drinks, meat, sausages, bread, rice cake, chocolate, candies, snacks, cookies, pizza, ramyun, noodles, gums, dairy products including ice cream, soups, beverages, tea, drinks, alcoholic drinks and vitamin complex, etc.

The present invention further provides a treating agent for erectile dysfunction containing an alcohol extract of ogalpi as an effective ingredient.

The extract of the present invention showed a strong relaxing effect on corpus cavernous smooth muscle of a rabbit, and increased the erectility of a white rat, dose- and administration time-dependently, when it was orally administered. Thus, the extract of the present invention can be effectively used as a treating agent for erectile dysfunction.

The improvement effect of an extract of the present invention on erectile dysfunction was investigated as follows; 500 mg of the ogalpi extract was put tightly in a capsule to make a pharmaceutical formulation for it, and then the produced medicine was orally administered to 48 patients suffering from erectile dysfunction for two months, three times a day and two capsules for one time administration, then an interview with each patient and questionnaire (about sexual desire, improvement of erectibility, satisfaction, etc) were conducted.

As a result, 72.9% (35 out of 48 patients) were experienced the improvement of erectility and none were experienced side effects with the exception of two patients with dyspepsia. Thus, a treating agent containing an extract of the present invention as an effective ingredient can be used for the improvement of erectile dysfunction.

An extract of ogalpi of the present invention can be included in a treating agent for erectile dysfunction by 1~100 parts of weight against the total parts of weight of the treating agent, and preferably by 50~100 parts of weight. One or more pharmaceutically acceptable carriers can be additionally added to make a pharmaceutical formulation containing the extract. The carrier can be selected from a group consisting of saline, buffered saline, water, glycerol and ethanol, but the selection is not always limited thereto. Any acceptable pharmaceutical formulation known in this field (Remington's Pharmaceutical Science (the newest edition), Mack Publishing Company, Easton Pa.) is available.

An ogalpi extract of the present invention can be administered orally and be used in general forms of pharmaceutical formulations. The extract of the present invention can be prepared for oral administration by mixing with generally used fillers, extenders, binders, wetting agents, disintegrating agents, diluents such as surfactant, or excipients.

The effective dosage of the extract of the present invention can be determined according to age, gender, health condition, absorption of an active ingredient, inactivation rate, excretion and other medicines applied together. For example, the dosage for oral administration might be 1~1.5 g per day, but not always limited thereto. The present invention also includes pharmaceutical formulations in dosage units. This means that the formulations are present in the form of individual parts, for example tablets, coated tablets, capsules, pills, suppositories and ampoules, the active compound content of which corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is administered in one application and which usually corresponds to a whole, ½, ⅓ or ¼ of a daily dose.

Solid formulations for oral administration are tablets, pill, dusting powders and capsules, liquid formulation for oral administrations are suspensions, solutions, emulsions and syrups, and the above mentioned formulations can contain various excipients such as wetting agents, sweeteners, aromatics and preservatives in addition to generally-used simple diluents such as water and liquid paraffin.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of Ogalpi Extracts

In order to prepare ogalpi extracts, *Acanthopanax divaricatus* var. *albeofructus*, *Acanthopanax senticosus* var. *subin-*

*ermis* and *Acanthopanax koreanum* were obtained from Susin Ogapy Farm, Chonan, Korea, and *Acanthopanax senticosus* was collected in Chungok Mountain, Kangwon-Do, Korea. The roots and the stems were separated from each other and dried. After drying, they were cut into small pieces and put in 70% ethanol or distilled water, followed by extraction according to the standard of food and drug. Ogalpi extracts used in the present invention were classified according to the kinds of ogalpi and represented as follows; an extract of *Acanthopanax divaricatus* var. *albeofructus* was marked as H; an extract of *Acanthopanaz senticosus* was marked as K; an extract of *Acanthopanaz senticosus* var. *subinermis* was marked as M; and an extract of *Acanthopanax koreanum* was marked as S. More precisely, the groups were subdivided according to a part of the plants used for the extraction (stems (S), meaning all the aerial parts except roots, and roots (R)). Thus, each 70% ethanol extract of four different ogalpi was classified into HR, HS, KR, KS, MR, MS, SR, and SS. Likewise, each extracts prepared by using distilled water was classified into HSW, KSW, MSW, and SSW.

Example 2

Relaxing Effect of Ogalpi Extract on Corpus Cavernous Smooth Muscle of a Rabbit (In Vitro Test)

<2-1> Preparation of Slices of Corpus Cavernous Smooth Muscle of a Rabbit

85 New Zealand white male rabbits (Samtaco BIO KOREA, Osan, Kyunggido, Korea) at the age of 4-6 months were selected as test animals because they have similar erection mechanism and structure of corpus cavernous smooth muscle to that of human. 30-50 mg/kg of sodium pentobarbital was injected into auricular vein of rabbits to put them under anesthesia. The penis of the animal was cut out and corpus cavernous smooth muscle of it was separated in a low-temperature tyrode solution (composition: (mEq/L) $Na^+$ 153.6, $K^+$ 5.3, $Ca^{2+}$ 3.0, $Mg^{2+}$ 1.2, $Cl^-$ 157.2, $H_2PO^{4-}$ 0.6, $SO^{4-}$ 1.2, $HCO^{3-}$ 7.1 and glucose 5.0) supplied with a mixed gas of 95% $O_2$ and 5% $CO_2$. The separated corpus cavernous smooth muscle was sliced as thin as 2×2×6 mm, which was fixed in 10 ml organ bath containing tyrode solution. The movement of the corpus cavernous smooth muscle was recorded by isotonic contraction recorder (Biopac systems, Santa Barbara, Calif., USA) connected thereto. The temperature of tyrode solution in the organ bath was maintained at 37° C., and pH was set at 7.4 by the continuous supply of the $O_2$ mixed gas. The corpus cavernous smooth muscle was rubbed to get rid of endothelial cells (Kim N et al., *J Clin Invest*, 1991, 88, 238-42). The slices of corpus cavernous smooth muscle prepared above were contracted by phenylephrine (5×10-6 M; referred as "PHE" hereinafter) and then relaxation was induced by acetylcholine (Ach) to confirm whether or not endothelial cells were. When endothelial cells were completely removed, relaxation was not induced by acetylcholine or if it had been induced, it would have been within 10% of relaxing level shown before the elimination of endothelial cells. Therefore, such samples showing no response to acetylcholine or only a minor relaxation were selected, leading to the preparation of smooth muscle slices devoid of endothelial cells. Other experiments not related with endothelial cells were performed with general slices of corpus cavernous smooth muscle.

<2-2> Determination of Ideal Tension for Isotonic Contraction

Initial tension was kept as 2 g. After getting in a stable condition, PHE was injected to investigate the level of contraction. The slice of endothelial cell was washed with tyrode solution to recover the sable condition, and the level of contraction by the same PHE content was investigated under a stable condition controlled with the increase or the decrease of tension. When the level of contraction was under 10% of the prior contraction two times consecutively, it was determined to be an ideal tension, and drug response experiments were carried out under such stable and ideal tension.

<2-3> Effect of Ogalpi Extract on Tension of Corpus Cavernous Smooth Muscle

The stabilized corpus cavernous smooth muscle was treated with PHE by the concentration of $5 \times 10^{-6}$ M to induce contraction. Then, ogalpi extracts prepared in the above example 1 were administered by different concentrations (1 mg/ml, 2 mg/ml, 5 mg/ml or 10 mg/ml), and the movement of the corpus cavernous smooth muscle was recorded by the same method as described in the above example <2-1>.

Figure 1:
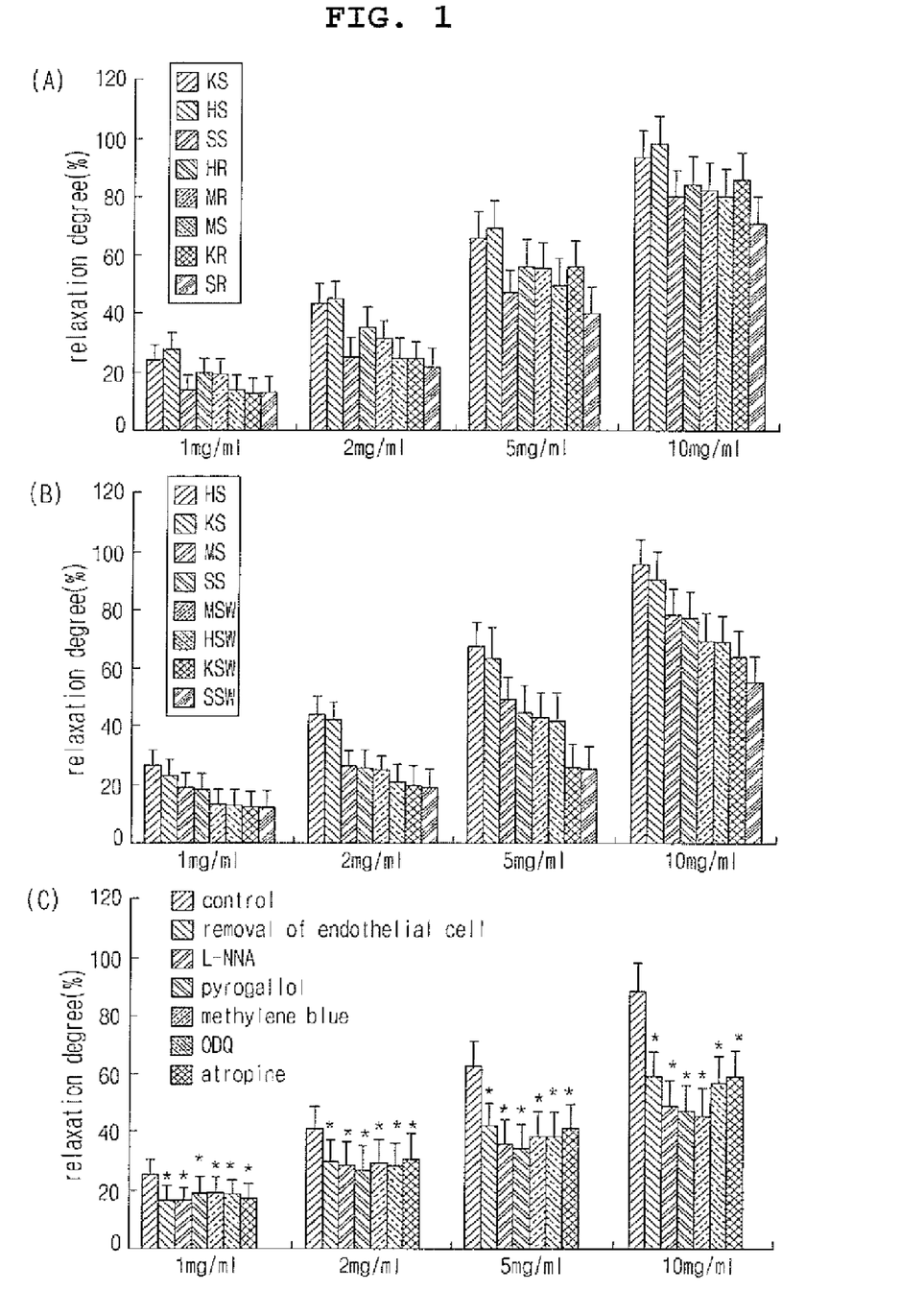
FIG. 1a is a graph showing the comparison of relaxing effects on corpus cavernous smooth muscle of a rabbit among 70% ethanol extracts extracted from roots or stems of *Acanthopanax divaricatus* var. *albeofructus*, *Acanthopanax senticosus*, *Acanthopanax senticosus* var. *subinermis* and *Acanthopanax koreanum*.
FIG. 1b is a graph showing the comparison of relaxing effects on corpus cavernous smooth muscle of a rabbit among extracts extracted from stems of *Acanthopanax divaricatus* var. *albeofructus*, *Acanthopanax senticosus*, *Acanthopanax senticosus* var. *subinermis*, and *Acanthopanax koreanum* by using distilled water or 70% alcohol.
FIG. 1c is a graph showing the effect of ODQ, methylene blue, pyrogallol, atropine, L-NNA or the removal of endothelial cells on the relaxation of corpus cavernous smooth muscle of a rabbit induced by 70% ethanol extract prepared from the stems of ogalpi (HS), In FIG. 1a~FIG. 1c,
KS: 70% ethanol extract of *Acanthopanax senticosus* stem,
HS: 70% ethanol extract of *Acanthopanax divaricatus* var. *albeofructus* stem,
SS: 70% ethanol extract of *Acanthopanax koreanum* stem,
MS: 70% ethanol extract of *Acanthopanax senticosus* var. *subinermis* stem,
KR: 70% ethanol extract of *Acanthopanax senticosus* root,
HR: 70% ethanol extract of *Acanthopanax divaricatus* var. *albeofructus* root,
SR: 70% ethanol extract of *Acanthopanax koreanum* root,
MR: 70% ethanol extract of *Acanthopanax senticosus* var. *subinermis* root.

As a result, in aspects of the extraction parts (S or R), the extracts of HR, HS, KR, MR, MS, SR and SS, which were extracted by using 70% ethanol from stems (S) and roots (R) of *Acanthopanax divaricatus* var. *albeofructus* (H), *Acanthopanaz senticosus* (K), *Acanthopanaz senticosus* var. *subinermis* (M), and *Acanthopanax koreanum* (S), showed relaxing effect on corpus cavernous smooth muscle of a rabbit dose-dependently from the dose of 1 mg/ml. When the levels of relaxation were compared, extracts prepared from S had better relaxing effect than those prepared from R, except the case of an extract of M. The best effect was observed in H extract, and followed by K, M, S, in that order, indicating that ES has the most powerful relaxing effect among all the ogalpi extracts (FIG. 1*a*). Thus, it was also proved by the result that the activity of extracts prepared form stems was the greatest.

Next, in aspects of the solvents, extracts extracted by 70% ethanol (HS, KS, MS, SS) showed higher relaxing effects than other extracts extracted by distilled water (HSW, KSW, MSW and SSW), and in particular, HS showed the highest relaxing effect (FIG. 1*b*).

<2-4> Analysis of the Relaxing Mechanism of Corpus Cavernous Smooth Muscle Induced by Ogalpi Extract In order to investigate whether or not NO was involved in relaxation of corpus cavernous smooth muscle, the slices of the muscle were contracted by PHE and then treated with $10^{-4}$ M of guanylate cyclase specific inhibitor 3 1H-[1,2,4]-oxadiazolo[4,3-Ip quinoxalin-1-one] (referred as "ODQ" hereinafter), $10^{-4}$ M of guanylate cyclase non-specific inhibitor methylene blue, $10^{-4}$ M of a NO inactivator pyrogallol, an oxygen free radical generator, and $3 \times 10^{-4}$ M of NO generation inhibitor NW-nitro-L-arginine (referred as "L-NNA" hereinafter), respectively. Then, the slices were treated with different concentrations of HS (an ogalpi extract) (1 mg/ml, 2 mg/ml, 5 mg/ml or 10 mg/ml) to measure the level of relaxation.

In order to investigate whether a cholinergic neurotransmitter was involved, the slices were treated with $5 \times 10^{-6}$ M of atropine, to which HS, an extract of ogalpi, was administered with different concentrations of 1 mg/ml, 2 mg/ml, 5 mg/ml or 10 mg/ml, to measure the level of relaxation.

In order to investigate the effect of endothelial cells on the relaxation induced by ogalpi extract, corpus cavernous smooth muscle devoid of endothelial cells was contracted by PHE, to which an ogalpi extract, HS, was treated with different concentrations of 1 mg/ml, 2 mg/ml, 5 mg/ml or 10 mg/ml to measure the level of relaxation.

As a result, the slices contracted by PHE began to be relaxed by HS dose-dependently from the concentration of 1 mg/ml, and precisely, the relaxation was 27.6+, −8.20% at 1 mg/ml, 45.2+, −16.37% at 2 mg/ml, 69.3+, −12.57% at 5 mg/ml and 97.8+, −6.93% at 10 mg/ml. The relaxing effect of HS on the slice of corpus cavernous smooth muscle contracted by PHE was significantly affected by the removal of endothelial cells and other medicines such as ODQ, methylene blue, pyrogallol, atropine and L-NNA ($p<0.05$).

In order to confirm the relation between relaxing effect of ogalpi extract and calcium, the slices of corpus cavernous smooth muscle were washed with calcium excluded potassium-rich depolarization solution to lower the tension of the muscle. When the tension was relieved to the minimum level, keeping its' balance, $10^{-3}$M of $CaCl_2$ was supplemented and the contraction of the muscle was observed. The other slices of the muscle were treated with ogalpi extract at different concentrations of 1 mg/ml, 2 mg/ml, 5 mg/ml or 10 mg/ml, after then $10^{-3}$ M of $CaCl_2$ was supplemented thereto, followed by the observation on the contraction. The results were compared each other.

As a result, in the case of supplementing $10^{-3}$ M of $CaCl_2$ to the calcium excluded potassium-rich depolarization solution, the level of tension of the muscle was 2.12+, −1.21 g. In the mean time, in the case of treating HS at the different concentration of 1 mg/ml, 2 mg/ml, 5 mg/ml and 10 mg/ml, the contraction by $CaCl_2$ was decreased 62.85%+, −11.58%, 43.00+, −7.60%, 24.44+, −6.80% and 12.5+, −5.42%, respectively ($p<0.05$).

Example 3

Effect of Ogalpi Extract on cGMP and cAMP Concentrations in Corpus Cavernous Smooth Muscle of a Rabbit (In Vitro Test)

After contracting corpus cavernous smooth muscle of a rabbit by PHE, ogalpi extract was administered thereto to induce relaxation. Under the maximum relaxation, tissues were immediately frozen and kept in −70° C. Then, enzyme immunoassay (EIA) was performed using cGMP and cAMP analyzing kit (BIOTRA cellular communication assays kit) (Amersham pharmcia biotech, Buckinghamshire UK) to measure the contents of cGMP and cAMP.

As a result, the concentrations of cGMP and cAMP were increased by the treatment of ogalpi extract, HS, dose-dependently in the slice of corpus cavernous smooth muscle contracted by PHE (FIG. 2).

The excel program was used to calculate mean values and standard deviations from all the results obtained through example 1 to example 4. Mann-Whitney U test or student's t test was performed to judge the significance among all the resultant values of groups. And simple regression test was performed to determine whether or not the change of tension of a smooth muscle according to the different concentrations is significant (when $p<0.05$, it was determined to be a significant change).

Example 4

Effect of Ogalpi Extract on the Penile Erection of a White Rat (In Vivo Test)

<4-1> Preparation of Ogalpi Extract

In the present invention, *Acanthopanax divaricatus* var. *albeofructus* was obtained from Susin Ogapy Farm, Chonan, Korea, and then the stems were dried. The dried stems were cut into small pieces and put in 70% ethanol for extraction. An extract thereby was prepared (HS) according to the standard of food and drug.

<4-2> Changes of Pressure Inside of Corpora Cavernosa of a White Rat Resulted from the Oral Administration of an Ogalpi Extract Sprague Dawley white male rats (250-350 g) were used. The rats were divided into two groups; a control and an experimental group treated with an ogalpi extract. The experimental group was orally administered with an ogalpi extract once a day by the dosage of 50, 100 or 200 mg/kg in physiological saline using a syringe, and the administration was continued for 2 weeks or for 4 weeks.

30-50 mg/kg of pentobarbital was injected in the abdominal cavity to put the rat under anesthesia. The abdomen was cut in the center and bladder and prostate were exposed. After locating main pelvic ganglia on the posterolateral of the prostate, pelvic nerve and corpora cavernous nerve in the basin were isolated. Platinum electrode was installed on corpora cavernous nerve, which was then connected to an electrical stimulator (STM100A, Biopac system, Santa barbara, Calif., U.S.A.). Prepuce was incised to expose corpora cavernosa. 26G needle was linked in the corpora cavernosa to measure the inside pressure of the corpora cavernosa. In order to check up the condition of systemic blood flow affected by a given electric stimulus or a medicine during the experiments, 22G angio needle was stationed inside the carotid artery and blood pressure was constantly measured by a transducer and a polygraph system. Systemic blood pressure and the inside pressure of corpora cavernosa were transmitted to a differential amplifier (DA100, Biopac system, U.S.A.) through Sorenson transpac (Abbott Critical Care System, U.S.A.), then measured by data acquisition (MP 100, Biopac system, U.S.A.), leading to the final analysis by a data analysis program (Acq-knowledge 3.2 program, Biopac system, U.S.A).

In order to evaluate the penile erection by nerve stimulation given to corpora cavernosa, the inside pressure of the corpora cavernosa was measured after nerve stimulation was given (frequency: 2 Hz, threshold: 2 Volt), which was then compared with the maximum inside pressure of corpora cavernosa.

Figure 3:
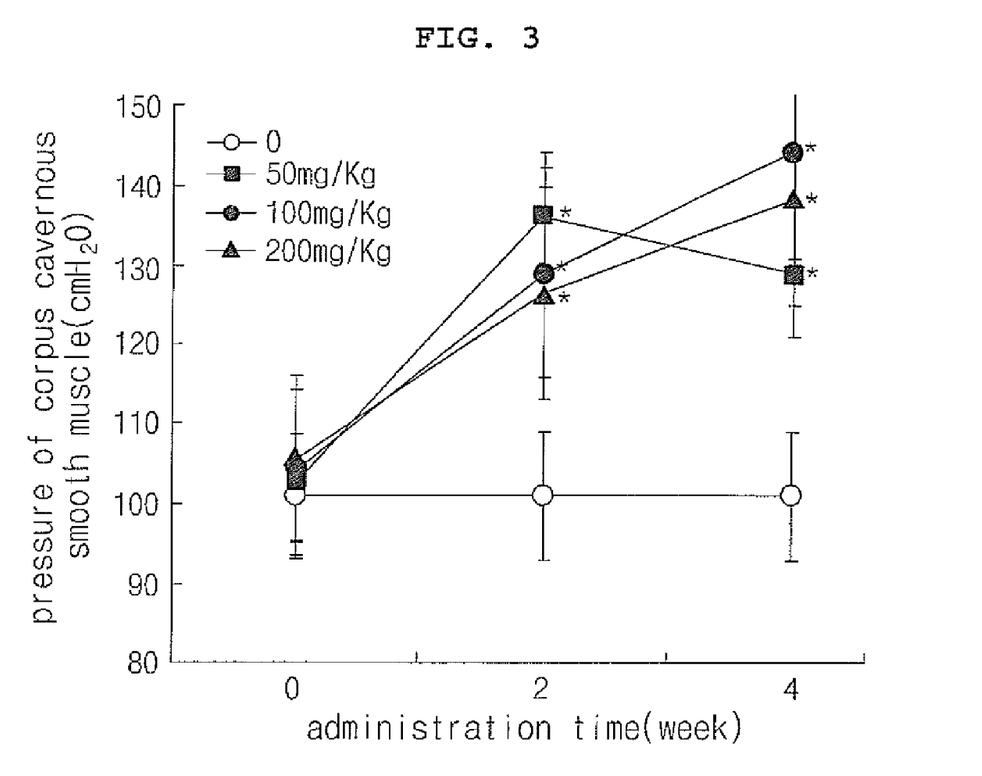
FIG. 3 is a graph showing the comparison of erectility between white rats orally administered with an extract (HS) extracted from the stems of *Acanthopanax divaricatus* var. *albeofructus* using 70% ethanol for 2 weeks and those administered for 4 weeks.

As a result, the penile erection was significantly improved ($p<0.05$) by the oral administration of HS, comparing to a control group. The erectility was varied from the dose and period of ES administration. When HS was administered for 2 weeks with the dosage of 50 mg/kg/day, the erectility was temporarily improved. In the mean time, when HS was administered for 4 weeks with the dosage of 100 mg/kg/day, the erectility was improved most. The erectility was increased with the extension of administration period (FIG. 3).

Example 5

Effect of Ogalpi Extract on cGMP and cAMP Concentrations in Corpus Cavernous Smooth Muscle of a White Rat (In Vivo Test)

The maximum penile erection was induced by nerve-stimulating corpus cavernous smooth muscle of a white rat. Under the condition of maximum erection, tissues were immediately frozen and stored at −70° C. Enzyme immunoassay (EIA) was performed using cGMP and cAMP analyzing kit (BIOTRA cellular communication assays kit) (Amersham pharmcia biotech, Buckinghamshire UK) to measure the contents of cGMP and cAMP.

As a result, the concentrations of cGMP and cAMP in corpus cavernous smooth muscle of a white rat were increased under erection in a control group in which nerve stimulation was given to the corpus cavernous smooth muscle. In the case of experimental group which was orally administered with HS by 100 mg/kg/day for 2 weeks or for 4 weeks, the contents of cGMP and cAMP were significantly increased ($p<0.05$), comparing to a control group, by nerve stimulation on corpora cavernosa under the condition of erection (FIG. 4). The above results indicate that the concentrations of cGMP and cAMP in corpus cavernous smooth muscle are increased with the long-term oral administration of ogalpi extract.

The excel program was used to calculate mean values and standard deviations from all the results obtained through example 1 to example 5. Mann-Whitney U test or student's t test was performed to judge the significance among all the resultant values of groups. And simple regression test was performed to determine whether or not the change of tension of a smooth muscle according to the different concentrations is significant (when $p<0.05$, it was determined to be a significant change).

Manufacturing Example 1

Preparation of Health Food Containing Ogalpi Extract

As explained hereinbefore, an ogalpi extract of the present invention has a strong improving effect on the erectile dysfunction. Thus, the present inventors prepared health food containing the ogalpi extract as an effective ingredient as follows.

<1-1> Preparation of Drinks

| | |
|---|---|
| Honey | 522 mg |
| Thioctic acid amide | 5 mg |
| Nicotinic acid amide | 10 mg |
| Sodium riboflavin hydrochloric acid | 3 mg |
| Pyridoxine hydrochloride | 2 mg |
| Inositol | 30 mg |
| Ortho acid | 50 mg |
| Ogalpi extract | 1.28 mg |
| Water | 200 ml |

Drinks were prepared based on the above compositions and contents by following a conventional method.

<1-2> Preparation of Chewing Gum

| | |
|---|---|
| Gum base | 20% |
| Sugar | 76.36~76.76% |
| Ogalpi extract | 0.24~0.64% |
| Fruit flavor | 1% |
| Water | 2% |

Chewing gum was prepared based on the above compositions and contents by following a conventional method.

<1-3> Preparation of Candy

| | |
|---|---|
| Sugar | 50~60% |
| Starch syrup | 39.26~49.66% |
| Ogalpi extract | 0.24~0.64% |
| Orange flavor | 0.1% |

Candy was prepared based on the above compositions and contents by following a conventional method.

<1-4> Preparation of Biscuit

| | |
|---|---|
| Strong flour 1$^{st}$ class | 88 kg |
| Cake flour 1$^{st}$ class | 76.4 kg |
| Refined sugar | 16.5 kg |
| Salt | 2.5 kg |
| Glucose | 2.7 kg |
| Palm shortening | 40.5 kg |
| Ammo | 5.3 kg |
| Baking soda | 0.6 kg |
| Sodium bisulfate | 0.55 kg |
| Rice flour | 5.0 kg |
| Vitamin B1 | 0.003 kg |
| Vitamin B2 | 0.003 kg |
| Milk flavor | 0.16 kg |
| Water | 71.1 kg |
| Whole milk powder | 4 kg |
| Substitute milk powder | 1 kg |
| Calcium phosphate, monobasic | 0.1 kg |
| Spraying salt | 1 kg |
| Spraying milk | 25 kg |
| Ogalpi extract | 0.2~0.5 kg |

Biscuit was prepared based on the above compositions and contents by following a conventional method.

<1-5> Preparation of Ice Cream

| | |
|---|---|
| Milk fat | 10.0% |
| Milk solids non-fat | 10.8% |
| Sugar | 12.0% |
| Starch syrup | 3.0% |
| Emulsifying stabilizer (span) | 0.5% |
| Flavor (strawberry) | 0.15% |
| Water | 63.31~62.91% |
| Ogalpi extract | 0.24~0.64% |

Ice cream was prepared based on the above compositions and contents by following a conventional method.

<1-6> Preparation of Chocolate

| | |
|---|---|
| Sugar | 34.36~34.76% |
| Cocoa butter | 34% |

-continued

| Ingredient | Amount |
| --- | --- |
| Cocoa mat | 15% |
| Cocoa powder | 15% |
| Lecithin | 0.5% |
| Vanilla flavor | 0.5% |
| Ogalpi extract | 0.24~0.64% |

Chocolate was prepared based on the above compositions and contents by following a conventional method.

<1-7> Preparation of Noodles Including Ramyun

A food composition was prepared by stirring 2 kg of mixture prepared by the compositions and contents listed in the below table 1 and 1.2 kg of dough solution together for 10~15 minutes using a firm dough-mixer with high span. The composition was shaped into noodles by extruder and then steamed. The steam was let off first and then the noodles were dried with a lyophilizer, resulting in dried noodles in the form of a final product. When the noodles are dried naturally, they are easily broken and become too tough to be boiled. But, when the noodles are prepared by lyophilization, they become soft enough to be boiled well and have their original shape without change, in addition to the good taste and active ingredients in them.

Ramyun can be prepared by the same method as used for the production of noodles above with the same ingredients. Just, the mold of extruder is different. After molding, ramyun is fried in oil or steamed. After steam is let off, ramyun is lyophilized, followed by packing.

TABLE 1

| Ingredient | Amount |
| --- | --- |
| Rice flour | 40 weight % |
| Wheat protein | 30 weight % |
| Flour | 15 weight % |
| Starch | 10 weight % |
| Rhynchosia nulubilis flour | 5 weight % |
| Water | 90 weight % |
| Ogalpi extract | 10 weight % |

<1-8> Preparation of Rice Cake 1 kg of dough solution and 2 kg of a mixture prepared according to the compositions and contents listed in the below table 2 were mixed and stirred for 10~15 minutes, which was then steamed to complete a target composition. The prepared composition was put in a mold of a bar rice cake or a rice cake with a flower pattern imprinted, followed by pressure molding, resulting in rice cake.

TABLE 2

| Ingredient | Amount |
| --- | --- |
| Rice flour | 60 weight % |
| Wheat protein | 30 weight % |
| Rhynchosia nulubilis flour | 7 weight % |
| Sugar | 2 weight % |
| Water | 90 weight % |
| Ogalpi extract | 10 weight % |
| Refined salt | Proper amount |

<1-9> Preparation of Bread 900 g of dough solution and 2 kg of a mixture prepared according to the compositions and contents listed in the below table 3 were mixed and stirred for 20 minutes, followed by fermentation at 35° C.~40° C. for 30 minutes. The resultant composition was molded in a wanted pattern and then steamed in an iron pot.

TABLE 3

| Ingredient | Amount |
| --- | --- |
| Rice flour | 30 weight % |
| Wheat protein | 30 weight % |
| Flour | 30 weight % |
| Rhynchosia nulubilis flour | 8 weight % |
| Oligosaccharide | 2 weight % |
| Water | 90 weight % |
| Ogalpi extract | 10 weight % |
| Refined salt, Powder, Yeast | Proper amount |

Manufacturing Example 2

Preparation of an Erectile Dysfunction Treating Agent Containing Ogalpi Extract as an Effective Ingredient The present inventors prepared an erectile dysfunction treating agent by the steps of preparing an ethanol extract from the stems of Acanthopanax divaricatus var. albeofructus, which was proved to have the best erectile dysfunction improving effect among all kinds of ogalpi, freeze-drying, pulverizing, and filling capsules by 500 mg per each capsule.

Example 6

Clinical Test of Ogalpi Extract as an Erectile Dysfunction Treating Agent

Clinical tests of an erectile dysfunction treating agent prepared in the above manufacturing example 2 were performed with patients suffering from erectile dysfunction. The number of patients was 48 and the average age of them was 43.4 (the oldest was 50 years old and the youngest was 36 years old). The administration method was oral administration, three times a day, and 2 capsules for one administration, which was continued for 2 months. The patient group consisted of 10 diabetics, 6 hypertension patients, 4 hyperlipidemia patients, 12 psychogenic impotence patients, 6 low-testosteron patients, and 10 unexplained impotence patients. Interviews with patients and questionnaire on sexual desire, the level of improvement of erectile dysfunction, satisfaction, etc, were performed to investigate the changes of the condition of erectile dysfunction.

As a result, erectile dysfunction was improved during the two-month oral administration in 72.9% patients (35 out of 48 patients), and almost no one had trouble with side effects, except only two patients with dyspepsia. Therefore, an erectile dysfunction-treating agent of the present invention was confirmed to have excellent improving effect on erectile dysfunction without side effects because it was prepared from a safe natural substance.

INDUSTRIAL APPLICABILITY

As explained hereinbefore, an ethanol extract extracted from the stems of ogalpi of the present invention has excellent relaxing effect on corpus cavernous smooth muscle and promoting effect of erectility, so that it can be effectively used for the production of health food, an aid to improve erectile dysfunction, or a treating agent for erectile dysfunction.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method of treating erectile dysfunction in a mammal comprising:
   administering an alcohol extract of stem or root of *Acanthopanax* to a mammal in need thereof,
   wherein the *Acanthopanax* is *Acanthopanax divaricatus* var. *albeofructus* or *Acanthopanax koreanum*.

2. The method as set forth in claim 1, wherein the *Acanthopanax* is *Acanthopanax divaricatus* var. *albeofructus*.

3. The method as set forth in claim 1, wherein the alcohol is methanol, ethanol, propanol or butanol.

4. The method as set forth in claim 1, wherein the alcohol is ethanol.

5. The method as set forth in claim 1, wherein the alcohol is 70% ethanol.

6. The method as set forth in claim 1, wherein the alcohol extract is administered in an amount of 1-1.5 g per day.

7. A method of relaxing corpus cavernous smooth muscle in a mammal, comprising:
   administering an alcohol extract of stem or root of *Acanthopanax* to a mammal in need thereof,
   wherein the *Acanthopanax* is *Acanthopanax divaricatus* var. *albeofructus* or *Acanthopanax koreanum*.

8. The method as set forth in claim 7, wherein the *Acanthopanax* is *Acanthopanax divaricatus* var. *albeofructus*.

9. The method as set forth in claim 7, wherein the alcohol is methanol, ethanol, propanol or butanol.

10. The method as set forth in claim 7, wherein the alcohol is ethanol.

11. The method as set forth in claim 7, wherein the alcohol is 70% ethanol.

12. The method as set forth in claim 7, wherein the alcohol extract of stem or root of *Acanthopanax* is administered in an amount of 1-1.5 g per day.

* * * * *